(12) United States Patent
Wall

(10) Patent No.: US 10,626,630 B2
(45) Date of Patent: *Apr. 21, 2020

(54) HYBRID OPERATING ROOM FOR COMBINED SURGICAL AND FIXED IMAGING SERVICES IN AN AMBULATORY SURGICAL CENTER

(71) Applicant: PM HOLDINGS, LLC, Paradise Valley, AZ (US)

(72) Inventor: L. Philipp Wall, Paradise Valley, AZ (US)

(73) Assignee: PM HOLDINGS, LLC, Paradise Valley, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/246,931

(22) Filed: Jan. 14, 2019

(65) Prior Publication Data
US 2019/0145117 A1    May 16, 2019

Related U.S. Application Data

(63) Continuation of application No. 15/138,134, filed on Apr. 25, 2016, now Pat. No. 10,180,008, and a
(Continued)

(51) Int. Cl.
| | |
|---|---|
| *E04H 3/08* | (2006.01) |
| *A61B 5/00* | (2006.01) |
| *A61B 5/05* | (2006.01) |
| *A61M 16/01* | (2006.01) |
| *A61G 13/00* | (2006.01) |

(Continued)

(52) U.S. Cl.
CPC .............. *E04H 3/08* (2013.01); *A61B 5/0071* (2013.01); *A61B 5/055* (2013.01); *A61G 13/00* (2013.01); *A61M 16/01* (2013.01); *G21F 7/00*
(2013.01); *A61B 6/4441* (2013.01); *A61B 6/4452* (2013.01); *A61B 6/4464* (2013.01);
(Continued)

(58) Field of Classification Search
CPC . E04H 3/08; G21F 7/00; A61G 13/00; A61M 16/01; A61B 5/055; A61B 5/0071; A61B 6/56; A61B 6/487; A61B 6/4464; A61B 6/4452; A61B 6/4441
USPC ........................................................ 52/173.1
See application file for complete search history.

(56) References Cited

U.S. PATENT DOCUMENTS

| | | | | |
|---|---|---|---|---|
| 8,144,948 | B2 * | 3/2012 | Krachman | ........... A61B 5/7445 |
| | | | | 382/128 |
| 8,320,991 | B2 * | 11/2012 | Jascob | ................... A61B 90/36 |
| | | | | 600/420 |

(Continued)

OTHER PUBLICATIONS

Office Action dated Dec. 18, 2019 issued by the Japanese Patent Office on related Japanese Patent Application No. 2017-548366.

*Primary Examiner* — Jeanette E Chapman
(74) *Attorney, Agent, or Firm* — Dickinson Wright PLLC

(57) ABSTRACT

An outpatient surgical center can include a hybrid operating room. The hybrid operating room can include at least one radiation shielded wall, a floor, and a ceiling. The hybrid operating room can also include an imaging device disposed in the hybrid operating room. The hybrid operating room can further include an operating table disposed in the hybrid operating room. A building for the outpatient surgical center can initially be constructed to conform to International Building Code (IBC) Class B standards.

24 Claims, 3 Drawing Sheets

Related U.S. Application Data continuation-in-part of application No. 14/560,721, filed on Dec. 4, 2014, now Pat. No. 9,334,664, and a continuation-in-part of application No. 14/560,789, filed on Dec. 4, 2014, now Pat. No. 9,322,188, and a continuation-in-part of application No. 14/219,880, filed on Mar. 19, 2014, now Pat. No. 9,249,588, said application No. 15/138,134 is a continuation-in-part of application No. 14/560,721, filed on Dec. 4, 2014, now Pat. No. 9,334,664, which is a continuation of application No. 14/219,880, filed on Mar. 19, 2014, now Pat. No. 9,249,588, said application No. 14/560,789 is a continuation-in-part of application No. 14/219,880, filed on Mar. 19, 2014, now Pat. No. 9,249,588.

(51) Int. Cl.
*G21F 7/00* (2006.01)
*A61B 5/055* (2006.01)
*A61B 6/00* (2006.01)
*A61N 5/10* (2006.01)

(52) U.S. Cl.
CPC ............... *A61B 6/487* (2013.01); *A61B 6/56* (2013.01); *A61N 2005/1094* (2013.01)

(56) References Cited

U.S. PATENT DOCUMENTS

| | | | |
|---|---|---|---|
| 10,528,840 B2 * | 1/2020 | Bailey | A61B 34/10 |
| 2005/0242276 A1 * | 11/2005 | Okazaki | A61K 51/1282 |
| | | | 250/251 |

* cited by examiner

HYBRID OPERATING ROOM FOR COMBINED SURGICAL AND FIXED IMAGING SERVICES IN AN AMBULATORY SURGICAL CENTER

CROSS-REFERENCE TO RELATED APPLICATION

This application is a continuation of U.S. patent application Ser. No. 15/138,134 (U.S. Pat. No. 10,180,008, as of Jan. 15, 2019), filed Apr. 25, 2016, which is a continuation-in-part of U.S. patent application Ser. No. 14/560,721 (U.S. Pat. No. 9,334,664, as of May 10, 2016), filed Dec. 4, 2014, the entirety of which is hereby incorporated herein by reference, which is a continuation U.S. patent application Ser. No. 14/219,880, filed Mar. 19, 2014. This application is also a continuation-in-part of U.S. patent application Ser. No. 14/560,721 (U.S. Pat. No. 9,334,664, as of May 10, 2016), filed Dec. 4, 2014, the entirety of which is hereby incorporated herein by reference, which is a continuation U.S. patent application Ser. No. 14/219,880, filed Mar. 19, 2014. This application is also a continuation-in-part of U.S. patent application Ser. No. 14/560,789, filed Dec. 4, 2014 (U.S. Pat. No. 9,322,188, as of Apr. 26, 2016), the entirety of which is hereby incorporated herein by reference, which is a continuation-in-part of U.S. patent application Ser. No. 14/219,880, filed Mar. 19, 2014. This application is also a continuation-in-part of U.S. patent application Ser. No. 14/219,880, filed Mar. 19, 2014 (U.S. Pat. No. 9,249,588, as of Feb. 2, 2016), the entirety of which is hereby incorporated herein by reference.

BACKGROUND

Field

Various medical centers, other than hospitals, may benefit from having combined surgical and fixed imaging services. For example, ambulatory surgical centers may benefit from having a hybrid operating room that combines such surgical and fixed imaging services.

Description of the Related Art

Combined surgical and fixed imaging services in an operating room have been provided only in hospital facilities. Hospital facilities are generally designed with a variety of special features to fulfill strict safety requirements that add significantly to the cost to build and operate the hospital facility. For example, hospitals are typically constructed to adhere to strict building codes. Hospitals, for example, are classified according to International Building Code (IBC) as Institutional Group I-2, meaning occupancy shall include buildings and structures used for medical care on a 24-hour basis for more than five persons who are incapable of self-preservation. Hospitals typically also have heightened requirements regarding fire control, such as specific required building materials, in part because the occupants of the hospital are often incapable of self-preservation, as noted above.

Furthermore, hospitals traditionally include a variety of equipment. Normally, a hospital includes a number of hospital beds. Similarly, hospitals typically include patient rooms, which may house those hospital beds, and patient restrooms. Often, the size of a hospital is given as the number of beds the hospital has. Furthermore, hospitals also often include other facilities, such as a pharmacy, a lab, a morgue, and facilities providing radiology services, infection isolation, dietary services, linen services, emergency services, and the like.

Additionally, hospitals normally are required to have disaster prevention provisions for the primary structure and services as well as a disaster response plan, policy, and capabilities. Likewise, in view of the size of hospitals, hospitals often include central services (for example, central sterilization services), materials management, environmental services, and engineering services.

According to conventional wisdom, combined surgical and imaging services in an operating room are best provided in a hospital context. For example, imaging equipment is often heavy and has substantial power requirements. Hospitals, with their massive infrastructure, can readily accommodate such requirements. Also, imaging equipment often requires shielding due to the use of radiation, such as x-rays. Again, the infrastructure of a hospital is conventionally thought to be the only medical facility infrastructure adapted to safely accommodate such a purpose. For example, the thick concrete walls and floors of a typical hospital can help to block radiation.

Operating rooms for providing combined surgery and fixed imaging in a hospital are comparatively large. For example, a typical combined surgical and fixed imaging surgery room in a hospital may be in the range of 800 to 1000 square feet. For example, operating rooms in a hospital need to be of such comparatively large size in order to accommodate the performance of up to twenty to thirty different surgical specialties and sub-specialties as may normally be performed in a hospital, such as cardiac, thoracic, vascular, obstetrics, gynecological, orthopedic, podiatric, urologic, otolaryngologic, neurosurgery, trauma, ophthalmology, gastrointestinal, transplant, general surgery, colorectal surgery, hand surgery, endocrine surgery, breast surgery, plastic surgery, head and neck surgery, surgical oncology, pediatric surgery, spine surgery, oral maxillo facial surgery and so on.

Furthermore, hospitals typically are required to have particularly robust infectious vector isolation as well as high quality and sophisticated nurse call systems. Hospitals also have requirements for control of airborne sound transmission and water temperature requirements. Hospitals also normally have medical gas systems with strict requirements on their number and amount of testing. Likewise, elevators in hospitals are required to be large to accommodate gurney traffic.

As mentioned above, hospitals typically have specific fire code requirements. For example, hospital construction materials must be non-combustible and must provide for patient and staff safety in case of an emergency. Because hospitals are viewed as essential in case of a disaster, hospitals must be able to withstand greater events, such as earthquakes, floods, and the like. The structure also needs to be designed to provide the option of defending the structure in place rather than evacuating the structure.

To support such objectives, hospitals may be required to have redundancy of critical services, such as heating, ventilation, and air conditioning (HVAC), power, water supply, water heating, and the like. Furthermore, the materials from which the building is constructed, including the finishes for interior walls and ceilings, must comply with strict fire requirements, such as a very low flame spread index. Other similar reinforcements and protections may likewise be required. In short, a hospital is normally required to have a significantly enhanced infrastructure.

By contrast, conventional ambulatory surgical centers (ASCs) can be constructed in office buildings. These buildings have various code requirements, but typically these requirements are much less strict, and therefore, can be fulfilled with significant cost savings as compared to the cost to build a hospital. For example, an IBC class B structure, which may house an ASC, will have significantly less strict construction requirements than an IBC class I-2 structure, typically associated with the construction of a hospital. Similarly, the air change requirements for ASCs and other requirements may be much less strict for ASCs than for hospitals. In this discussion, class B can refer to use and occupancy classification, such as described in International Building Code (2012 version), Chapter 3, section 304, "Business Group B."

Likewise, ASCs typically do not require a pharmacy, a lab, a morgue, linen services, dietary services, and the like. Indeed, ASCs normally do not have any hospital beds, because it is not expected that the patients will be staying overnight.

Similarly, typical operating rooms in ASCs may be smaller than in hospitals. For example, an operating room in an ASC may be less than 600 square feet and possibly as small as 425 square feet. Furthermore, an ASC may generally offer only one to ten different surgical specialties, rather than the twenty to thirty surgical specialties offered in a typical hospital.

ASCs can herein or otherwise be described in various ways. For example, ASCs can also be referred to as ambulatory surgery center, clinics, outpatient surgical centers, and the like. Thus, herein or otherwise the term ASC can refer generally to ASCs, clinics, outpatient surgical centers and similar structures.

Office-based labs (OBLs) are another kind of non-hospital building in which medical procedures may be performed. OBLs may be limited as to the type of procedures that can be performed. For example, general anesthesia cannot be provided in an office setting in most states. Additionally, an office may lack the ability to provide an environment that prevents infection. Likewise, the use of an OBL may be limited to the physician's specialty of practice.

As an example, safely placing a patient in a prone position on the operating room table may not be possible in an office, as the ability to protect the airway is significantly impaired and may require placement of a breathing tube. Such placement of a breathing tube may, for safety reasons, require an ambulatory surgery center.

Most procedures performed in an OBL do not require general anesthesia, can be performed without an incision and are relatively short in duration. OBLs are typically established by cardiologists and pain groups, as their procedures do not require general anesthesia and may be performed percutaneously. Because OBLs do not require separate licensure they are not required to have back up power resources to permit continued surgery and recovery of patients. Moreover, such OBLs can include procedure rooms, as opposed to operating rooms, with typically one procedure room.

Typically a given OBL would be used by a limited number of physicians focused on a specific area of medicine: pain, cardiology, and so on. In addition, registered nurses are not required in the care of a patient in such an environment. Given that separate licensure is not required, the design of an OBL is not reviewed by a licensing body and is dictated by the space of the physician's environment and needs. It is not unusual for a medical practice to combine several exam rooms into a procedure room.

Since most OBLs have procedure rooms, they have structural and environmental differences from an operating room as defined in "Guidelines for Design and Construction of Hospitals and Outpatient Facilities."

Operating rooms may have various differences from procedure rooms. Operating rooms are typically located in a restricted area, have monolithic floors, walls and ceilings that are scrubbable and resistant to cleaning chemicals, have their own dedicated air handlers to prevent recirculation of air, have positive pressure ventilation to prevent entry of external air into the operating room, and have back up power to permit continuity of surgery in the operating room. Procedure rooms are typically located in an un-restricted or semi-restricted area, tend to have drop grid ceilings, may have tiled flooring, typically do not have a separate air handler, and have no specific ventilation requirements.

The national practitioner identifier program identifies ASCs with a separate taxonomy. ASCs have a specific taxonomy code of 261QA1903X as specified in the National Provider Identifier (NPI) by the Centers for Medicare and Medicaid Services (CMS) under the National Plan and Provider Enumeration System (NPPES). General Acute Care Hospitals have the taxonomy code of 282N00000X. Physicians' offices, OBLs, and Independent Diagnostic Testing Facilities (IDTFs) have taxonomy codes specific to their specialty such as Family Medicine—207Q00000X, Internal Medicine—207R00000X, Cardiovascular Disease—207RC0000X, Diagnostic Radiology—2085R0202X. ASCs are also distinguished by their place of service code "24", whereas as hospitals are place of service code "22", and an office is place of service code "11".

SUMMARY

According to certain embodiments of the present invention, an outpatient surgical center can include a hybrid operating room. The hybrid operating room can include at least one radiation shielded wall, a floor, and a ceiling. The hybrid operating room can also include an imaging device disposed in the hybrid operating room. The hybrid operating room can further include an operating table disposed in the hybrid operating room. A building for the outpatient surgical center can initially be constructed to conform to International Building Code (IBC) Class B standards.

In certain embodiments of the present invention, a method of manufacturing an outpatient surgical center can include building a hybrid operating room. The hybrid operating room can include at least one radiation shielded wall, a floor, and a ceiling. The method can also include shielding the at least one wall with radiation shielding. The method can further include installing an imaging device disposed in the hybrid operating room. The method can additionally include installing an operating table disposed in the hybrid operating room. The building can include constructing the outpatient surgical center from a building initially constructed to conform to International Building Code (IBC) Class B standards.

A building, according to certain embodiments of the present invention, can include a hybrid operating room. The hybrid operating room can include radiation shielding. The hybrid operating room can also include an imaging device disposed in the hybrid operating room. The hybrid operating room can further include an operating table disposed in the hybrid operating room. The building can include 50,000 square feet or less of floor space.

A building, in certain embodiments of the present invention, can include a hybrid operating room. The hybrid operating room can include radiation shielding. The hybrid operating room can include an imaging device disposed in the hybrid operating room. The hybrid operating room can also include an operating table disposed in the hybrid operating room. The building can include an outpatient surgical center.

An outpatient surgical center can include, according to certain embodiments, a plurality of hybrid operating rooms connected by a hallway. Each hybrid operating room of the plurality of hybrid operating rooms can include at least one radiation shielded wall, a floor, and a ceiling. Each hybrid operating room of the plurality of hybrid operating rooms can include an imaging device disposed in the hybrid operating room. Each hybrid operating room of the plurality of hybrid operating rooms can include an operating table disposed in the hybrid operating room.

BRIEF DESCRIPTION OF THE DRAWINGS

For proper understanding of the invention, reference should be made to the accompanying drawings, wherein.

DETAILED DESCRIPTION

According to certain embodiments of the present invention, combined surgical and fixed imaging services in an operating room can be provided in an ambulatory surgical center, outpatient surgical center, or the like, which can be collectively referred to as an ambulatory surgical center (ASC).

A difference between an ASC and a medical office, such as a doctor's office, may be the ability to charge a facility fee for reimbursement of use of the ASC. Another difference may be the ability to obtain Medicare accreditation as an ASC according to a government, for example the ability to obtain Medicare accreditation under the federal definition of an ASC. Similarly, a further difference may be the ability to obtain a license as an ASC and/or to obtain architectural review/approval of the building as an ASC. Licensure and architectural review/approval may be state dependent. In contrast with an ASC, there may not be specific design requirements for a medical office in which surgery may be performed. In certain cases, non-Medicare insurances may recognize a particular facility as an ASC for reimbursement purposes, unlike a medical office in which surgery may be performed.

Typical building differences from a medical office may be that ASCs for Medicare and for most states may be required to meet Medicare life safety codes and American Institute of Architects (AIA) guidelines, whereas medical offices may have no such requirements. Other guidelines may include the Facility Guidelines Institute (FGI) "Guidelines for Design and Construction of Hospitals and Outpatient Facilities" from 2010 or the update of those guidelines in 2014. Other standards may include National Fire Protection Association (NFPA) codes.

There may be other differences. For example, the ceilings of the operating rooms in an ASC may be monolithic.

Figure 1:
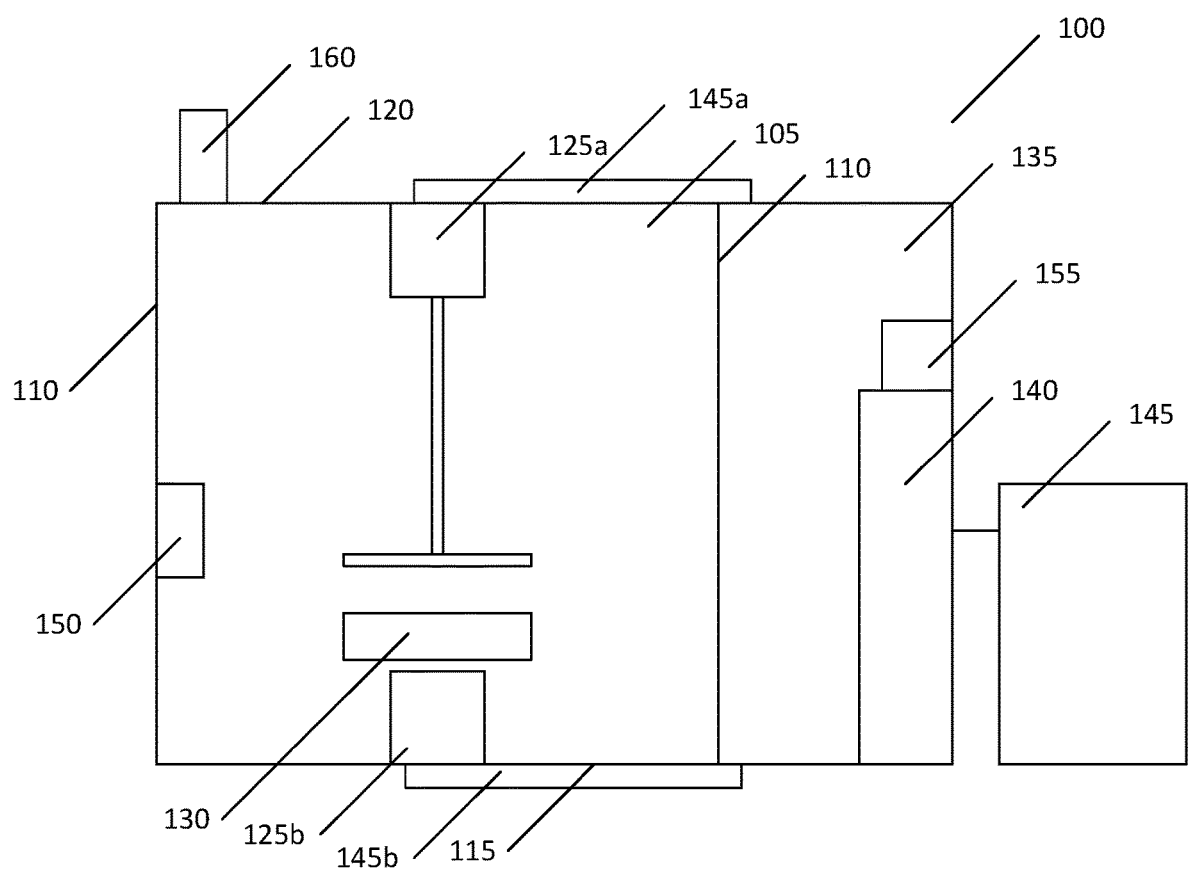
FIG. 1 illustrates a cross-section of an ambulatory surgical center according to certain embodiments of the present invention.

FIG. 1 illustrates a cross-section of an ambulatory surgical center according to certain embodiments. As shown in FIG. 1, an ambulatory surgical center 100 can include a hybrid operating room 105. The hybrid operating room 105 can include one or more lead-shielded walls 110. Only two walls are shown in the cross-section view, but two more may be orthogonal to those illustrated. The hybrid operating room may also include a floor 115 and a ceiling 120. Shielded doors, not illustrated, may also be provided in the lead-shielded walls. Other shielding materials besides lead are also permitted in certain embodiments. Those doors may lead to a hallway or to other rooms including additional hybrid operating rooms.

There can be lead-shielded walls 110, which are shielded to a height of less than a predetermined limit, e.g., eight feet. Thus, the lead-shielded walls 110 may be shielded to a height that is lower than the height of the ceiling 120, such as to a height of at least seven feet. Other heights are also permitted. The ceiling 120 may not, in certain embodiments, include lead shielding or any other type of radiation shielding. This may be particularly applicable when the ambulatory surgical center 100 is a single story building or when the ambulatory surgical center 100 is on the top floor of an office building. By contrast, in other embodiments the ceiling 120 may be shielded. For example, such shielding may be provided when the ambulatory surgical center 100 is located on a lower floor of a multi-story building.

Similarly, the floor 115 can be shielded or unshielded, according to the location of hybrid operating room 105 with respect to the rest of the ambulatory surgical center 100 or building. For example, when the ambulatory surgical center 100 is on a second floor, the floor 115 may be shielded (with lead or other radiation shielding material), whereas when the ambulatory surgical center 100 is on a ground floor or in a basement, it may not be necessary to shield the floor 115. In a basement it may not be necessary to provide any additional shielding to one or any of the walls.

In certain embodiments, the floor 115 may be reinforced. For example, if a multistory building is used, and the hybrid operating room 105 is installed in a second story of the building, the floor 115 of the hybrid operating room 105 may be modified in various ways, such as to provide conduits or shielding, but also to provide additional support for imaging or other equipment in the hybrid operating room 105.

A material can be considered as shielding if it provides adequate protection to humans who are on the side opposite the material from the radiation source. The adequacy of the protection may depend on factors such as what is deemed a safe exposure level and depending on an expected dwell time of a human on the other side of the shielding. The adequacy of the protection may also depend on the type of radiation used in the imaging. For example, in the case of MRI, copper shielding may be suitable because radio frequency is the type of radiation being used.

The ambulatory surgical center 100 can also include an imaging device 125a, 125b disposed in the hybrid operating room 105, for example in a central area of the hybrid operating room 105. The ambulatory surgical center 100 can further include an operating table 130 disposed in the hybrid operating room 105, for example in the central area of the hybrid operating room 105. The operating table 130 is shown without legs due to the cross-sectional view, but the operating table 130 may have legs, wheels, or the like. The operating table 130 may be in a fixed position or may be capable of movement, for example, to position a patient.

The imaging device 125a, 125b can be or include a fluoroscopy device. The fluoroscopy device can include a fixed C-arm device with the ability to perform, among other things, cineradiography (CINE) and digital subtraction. A CAT scan or MRI device may be used instead of or in addition to a fluoroscopy device as an imaging device. The imaging device 125a, 125b can include a radiating component 125b fixed to the floor 115 or ceiling 120 and a monitor component 125a fixed to the ceiling 120. Alternatively, the monitoring component 125a can be fixed to the floor 115. In other embodiments the monitoring component 125a and the radiating component 125b, or either of the components, can be fixed to one or more of the walls.

The ambulatory surgical center 100 can further include an equipment room 135 adjacent to the operating room. The equipment room 135 can include a power supply 140 for the imaging device 125a, 125b. The ambulatory surgical center 100 can include one or more conduit(s) 145a, 145b from the equipment room 135 to the imaging device 125a, 125b configured to deliver power to the imaging device 125a, 125b.

A power room may broadly refer to any room with power electronics, power conditioning, or the like. In certain embodiments, a power room can also be an equipment room, for example, a room in which various equipment may be provided in association with the operating room including any device used in the operating room. Alternatively, a power room may be distinct from an equipment room. Thus, portions of the electronics for the imaging device 125a, 125b may be provided in cabinets (or in other arrangements) in equipment room 135. The equipment room 135 may include a step-down transformer, filters, uninterruptable power supplies, or other equipment that may support the use of the operating room. This equipment room 135 may be in addition to a room in the building into which a main electrical line for the building comes and from which the main electrical line is branched out to various parts of the building. This additional room may provide circuit breakers for the building, for example. This additional room can also be considered a power room, but may—in certain embodiments—be in addition to equipment room 135.

The conduit(s) 145a, 145b can be located beneath the floor 115 (for example, at 145b), above ground, or above the ceiling 120 (for example, at 145a). An above-ceiling conduit 145a may provide power to elements that are not attached to the floor (such as monitor element 125a), while the below floor-surface conduit 145b can provide power to elements that are attached to the floor (such as radiating component 125b), or which are held in place by gravity. An in-wall conduit (not shown) can likewise be used for equipment, for example if the equipment is attached to a wall. The conduit(s) 145a, 145b can also provide one or more data paths to imaging equipment or other computers in the hybrid operating room.

The equipment room 135 and/or the power supply 140 can be configured to provide power employing a variety of possible voltages. In certain embodiments, the equipment room 135 and/or the power supply 140 can be configured to provide power employing at least 480 VAC or at least 208 VAC. In other embodiments, the equipment room 135 may provide 120 VAC. Other voltages are also permitted. Furthermore, the equipment room 135 may include a step-up transformer 155 configured to provide the desired power, such as the 480 VAC, 208 VAC or any other desired power. A step-down transformer, not illustrated, may also or alternatively be provided. Other power conditioning or reliability circuitry, such as filters, uninterruptible power supplies, generators, or the like may also be provided. The equipment room may be configured to house computer equipment and may be provided with one or more conduits to the hybrid operating room or to another room in the building, such as to a room housing circuit breakers for the building.

In certain embodiments, the power may come directly from a room housing the circuit breakers. Likewise, in certain embodiments the step-up transformer 155 may be provided in a room housing the circuit breakers.

The ambulatory surgical center 100 can additionally include an emergency power source 145 for the imaging device 125a, 125b configured to permit continuity of surgery in the hybrid operating room 105 during a power outage. The emergency power source 145 may be, for example, a generator, an uninterruptable power supply, or another source of power different from the power used in a non-emergency setting. The emergency power source 145 may be configured to supply emergency power to other devices or aspects than just the imaging device 125a, 125b. For example, the emergency power source 145 may be configured to supply a critical power bus or critical power panel for multiple devices. The emergency power source 145 may be optional, and, in certain embodiments, may provide one or more levels of quality of emergency power. For example, the emergency power source 145 may provide a first level of quality of emergency power sufficient to permit safe shutdown of administrative or non-essential computer systems, and a second level of quality of emergency power sufficient to permit a safe conclusion of surgery relying on one or more computer system, robotics system, medical system, and/or imaging system.

The ambulatory surgical center 100 can also include equipment 150 configured for the supply and provision of medical gasses. The medical gasses can include anesthetic gasses, such as nitrous oxide, as well as oxygen. The medical gasses equipment 150 can also provide suction. Accordingly, the medical gasses equipment 150 can be attached to plumbing in the wall (not illustrated), as well as to a waste trap (not illustrated). In certain embodiments of the present invention, this plumbing may lead to a central medical gas room, from which gas and suction are provided to a plurality of hybrid operating rooms like hybrid operating room 105.

The ambulatory surgical center 100 can further include an air change system 160. The air change system 160 can be configured to provide a minimum or maximum number of air changes per hour or any desired air change rate therebetween. For example, the minimum number of air changes per hour may, in certain embodiments of the present invention, be six, ten, fifteen, or twenty room air changes per hour or any other desired rate.

The air change system 160, equipment 150 for the supply and provision of medical gases, equipment room 135, emergency power source 145, and conduits 145a, 145b may be configured to support a plurality of operating rooms. For example, an equipment room 135 may be located between two or amongst three or more operating rooms. In other embodiments, each operating room may have its own dedicated equipment room 135.

Other rooms may also be provided. For example, a control room can be provided. The control room may be used by ancillary staff. The control room may be shielded from radiation produced in the hybrid operating room. The room can include a leaded glass window or other ways of permitting the ancillary staff to view the hybrid operating room. For example, a closed circuit television system may be installed in the hybrid operating room with communications channel(s) provided to the control room.

Other equipment may be used as well. For example, a robotic c-arm may be used. This robotic c-arm may be controlled from the control room, in certain embodiments. In certain embodiments, the monitor portion of the imagining equipment may be provided in a control room or other remote location, either instead of or in addition to having the monitor portion provided in the operating room. Such a setup may be used in cases where the hybrid operating room is being used in combination with various telemedicine techniques.

The ambulatory surgical center 100 can include a wooden frame building structure. For example, the ambulatory surgical center 100 can be constructed according to building codes that are suitable to an office building. For example, the ambulatory surgical center 100 can be constructed to conform to International Building Code (IBC) Class B standards (or such other standards permitting the use of combustible construction materials). In certain embodiments, the building may initially be constructed according to Class B standards but may subsequently be modified to other standards, in whole or in part. In certain cases, a class I structure may be used as an ambulatory surgical center.

Various embodiments of the present invention may include a variety of options. For example, a building according to certain embodiments may include an ambulatory surgical center or medical office. The ambulatory surgical center or medical office can include at least one hybrid operating room, and optionally several hybrid operating rooms. The hybrid operating room(s) can each include at least one wall that is configured to shield radiation, a floor, and a ceiling.

Each hybrid operating room can include an imaging device disposed in a central area of the hybrid operating room. An MRI, CT scan, or similar device can be the imaging device. Rather than, or in addition to the imaging device, the room can include a device such as a gamma knife.

Each hybrid operating room can include an operating table disposed in the central area of the hybrid operating room. Optionally, one or more additional operating tables can be provided in the central area.

The ambulatory surgical center or medical office can include a power room/equipment room adjacent to the operating room. Alternatively, the power room and/or equipment room can be nearby the operating room, such as one or two rooms away from the hybrid operating room. The power room and/or equipment room can include a power supply for the imaging device.

The ambulatory surgical center or medical office can include a conduit from the power room/equipment room to the imaging device configured to deliver power to the imaging device. The conduit can also or alternatively include control cabling, data cabling, or other cabling.

The ambulatory surgical center or medical office can further include a conduit from the equipment room and/or power room to a control room and/or control desk. The conduit can include control cabling, data cabling, or other cabling. For example, the conduit can carry a video signal corresponding to a monitor of the imaging device. Thus, the conduit can be a conduit from the imaging device to the control room and/or control desk.

The ambulatory surgical center and/or medical office can also include, above the ceiling, structural support for the weight of a surgical light, imaging device, suspension of lead shielding to protect the operating physician from radiation, contrast injectors, and/or boom.

The ambulatory surgical center and/or medical office can also include a monolithic ceiling that is scrubbable and resistant to chemical cleaners. The ceiling can be equipped with cleaning equipment, such as radiators, sprayers, ultraviolet (UV) lights, or the like.

The ambulatory surgical center and/or medical office can also include a monolithic floor that is scrubbable and resistant to chemical cleaners. The monolithic ceiling and/or the monolithic floor can also be resistant to other kinds of cleaners, such as gamma radiation or ultraviolet light.

The ambulatory surgical center and/or medical office can include emergency power source. The emergency power source can be configured to provide power for any additional equipment in the room necessary to continue surgery such as surgical lighting, anesthesia equipment, air conditioning, heating, monitors, and so on, in addition to the imaging device itself.

The ambulatory surgical center and/or medical office can be a single story building. For example, the ambulatory surgical center and/or medical office can be initially constructed as a single-story office building. The ambulatory surgical center can be a freestanding building as opposed to a multi-tenant building.

The ambulatory surgical center and/or medical office can be provided in a building composed of combustible materials or built with substantial amounts of such materials. For example, the ambulatory surgical center and/or medical office may be a wood-frame building. The building may be a class III, IV, or V IBC construction type. The building may be from, for example, about 4,000 square feet to about 20,000 square feet.

The building can be designed for the occupants to stay for less than 24 hours. The building can be designed to facilitate evacuation in case of fire or other emergency, as opposed to being designed to permit sheltering in place.

The building may be built or modified such that a license is obtained to operate as an ASC.

The building can include two or more hybrid operating rooms. The rooms can be configured such that if there is an equipment failure in one room, a medical procedure can be transferred to the other room to avoid cancellation of the procedure.

Other buildings and construction types can also be used. For example, modular buildings or other prefabricated buildings, including buildings delivered as trailers such as double-wide trailer may be usable in certain embodiments. In such cases, the shielding requirements may depend on the location where the modular building is going to be installed. In certain embodiments, the modular building without radiation shielding installed can be shipped to a location and the radiation shielding can subsequently be added. In other embodiments, the radiation shielding can be installed in the modular building prior to shipping them to a final installation location. Although such buildings may be modular and may be delivered by trailer, the buildings may be stationary and fixed in position once they are finally assembled and deployed.

For example, in certain embodiments, the ambulatory surgical center can be adjacent to an office such as a medical office and separated from the office by at least one firewall. Thus, for example, in certain embodiments a firewall and other upgrades can be added to an existing office building or to a building otherwise constructed as suitable for office building usage. In certain embodiments, the ambulatory surgical center may, for example, be in a strip mall or in another structure where a wall is shared with another business, which business may not have anything to do with medical care. For example, the other office may be restaurant and the firewall may separate the ambulatory surgical center or part of that center from the restaurant. In other cases, an ambulatory surgical center may be separated from a related medical office or other parts of a building not related to the ambulatory surgical center, by a firewall.

In certain embodiments of the present invention, the ambulatory surgical center 100 may not be adjacent to or within a hospital. Indeed, in certain embodiments of the present invention, the ambulatory surgical center 100 may not be in close physical proximity to a hospital. Additionally, the ambulatory surgical center 100 may not be affiliated with any hospital.

The ambulatory surgical center 100 may not itself be a hospital. Furthermore, the ambulatory surgical center 100 can exclude an inpatient room configured to permit a patient to stay for more than twenty-three hours. The ambulatory surgical center may not include any rooms equipped with hospital beds. Similarly, the ambulatory surgical center 100 can be operated by medical professionals and medical support staff exclusively dedicated to providing not more than a predetermined number of surgical specialties, e.g., 5 or 10 or any number there between, of medical procedures in the ambulatory surgical center 100. Furthermore, the ambulatory surgical center 100 can be 50,000 square feet or less of floor space, for example, 40,000 or 20,000 square feet or less in terms of its floor space. Moreover, in certain embodiments, the hybrid operating room can be installed in a building that has 50,000 square feet or less of floor space, for example, 40,000 or 20,000 square feet or less, but which may not necessarily be an ambulatory surgical center.

Figure 2:
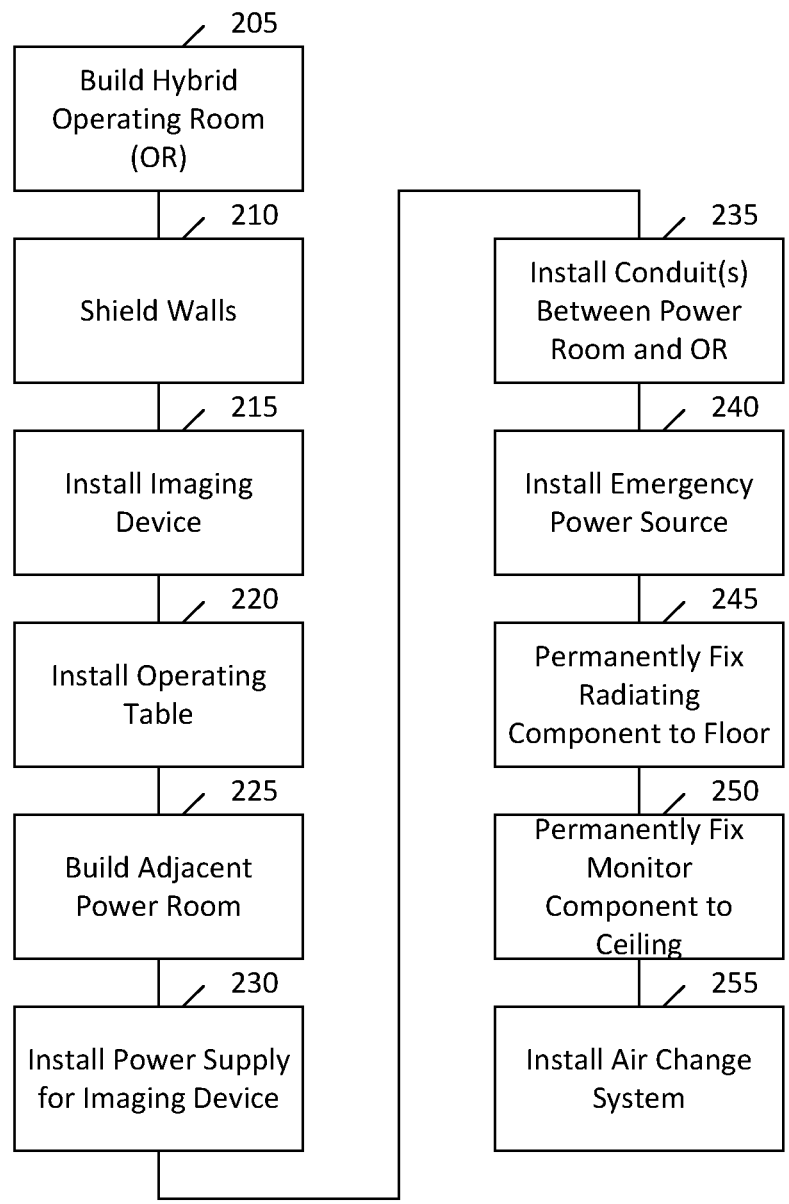
FIG. 2 illustrates a method of manufacturing an ambulatory surgical center, according to certain embodiments of the present invention.

FIG. 2 illustrates a method of manufacturing an ambulatory surgical center, according to certain embodiments of the present invention. The method can include, at 205, building a hybrid operating room. The hybrid operating room can include one or more lead-shielded wall, a floor, and a ceiling. The building of the hybrid operating room can involve converting an existing room into a hybrid operating room through renovations, or can involve building the hybrid operating room during construction of a building housing the hybrid operating room.

The method can also include, at 210, shielding the walls with lead or any other suitable shielding material. The lead shielded walls can be shielded to a height of less than a predetermined limit, e.g., eight feet. The shielding may, in certain embodiments, extend to a height of at least seven feet. The ceiling can be unshielded. The floor can also be unshielded, for example, when the ambulatory surgical center is on the ground floor of a building that does not have any basement or other space intended for human occupancy.

Other shielding scenarios are also possible. For example, if humans are not normally expected to be on the other side of a wall while the hybrid operating room is in use, the walls may be unshielded. For example, if there were landscaping without any walkways on the other side of the wall, or if the hybrid operating room is above ground level and there is no other nearby multi-story building, in such cases shielding may be omitted from such a corresponding wall.

The method can further include, at 215, installing an imaging device disposed in a central area of the hybrid operating room. The imaging device can be or include a fluoroscopy device. The fluoroscopy device can be a fixed C-arm device. A computed tomography (CAT or CT) scan or magnetic resonance imaging (MRI) device may be used instead of a fluoroscopy device as an imaging device. Other imaging devices are also permitted.

The method can additionally include, at 220, installing an operating table disposed in the central area of the hybrid operating room. The operating table can be installed and positioned specifically to place a patient within an operational range of the fluoroscopy device.

The method can further include, at 225, building an equipment room adjacent to the operating room. The building of this equipment room can be a matter of renovating an existing office building structure, in certain cases. The building can involve constructing the ambulatory surgical center from a building initially constructed to conform to International Building Code (IBC) Class B standards, such as the 2012 version of those standards or any similar standards. In certain embodiments, after renovation the portion of the building including the hybrid operating room may meet higher or stricter building standards.

The method can also include, at 230, installing, in the equipment room, a power supply for the imaging device. The power supply may be installed to receive electricity from an electric utility company (or from any other power source, such as self-generation, diesel generator, photovoltaics, or the like), process it, and supply it to the imaging device. The equipment room and/or power supply can be configured to provide power at, for example, 480 VAC. As mentioned above, other voltage values are also possible.

The method can additionally include, at 235, installing one or more conduit(s) configured to supply power from the equipment room to the imaging device. These conduits can be installed beneath the floor of the hybrid operating room and/or in or above the ceiling of the hybrid operating room. The conduits can additionally or alternatively be provided in at least one wall. The conduit may supply power at a lower or different voltage than is used or received in the equipment room.

The method can further include, at 240, installing an emergency power source for at least the imaging device configured to permit continuity of surgery in the hybrid operating room during a power outage. This emergency power source, if it is a generator or a set of batteries, may be installed outside the walls of the ambulatory surgical center, and may be connected by tie-ins to the equipment room and/or power supply.

The ambulatory surgical center can include a wooden frame building and can be constructed to conform to International Building Code (IBC) Class B standards (or such other standards permitting the use of combustible construction materials), as described above with reference to FIG. 1. Other constructions of the frame of the building are also permitted. For example, the ambulatory surgical center can include a steel, concrete, or masonry frame building structure.

The method can also include, at 245, permanently fixing a radiating component of the imaging device to the floor and, at 250, permanently fixing a monitor component of the imaging device to the ceiling. The monitor component and the radiating component may each include moving parts, but may be anchored to a specific location in the floor and ceiling.

The method additionally may include, at 255, installing an air change system in the ambulatory surgical center, wherein the air change system is configured to provide twenty room air changes per hour (or any other desired rate of air change).

The above method steps are described and illustrated in a particular order. Nevertheless, this order is simply for ease of reading and does not imply that the steps must be performed in the listed order. For example, the installation of the emergency power source may not need to have any particular order with respect to the other steps. Steps that must be performed under the floor, in the walls, or above the ceiling may be performed prior to the installation of the imaging equipment and operating table. Thus, the order of steps may be varied as desired or needed.

Figure 3:
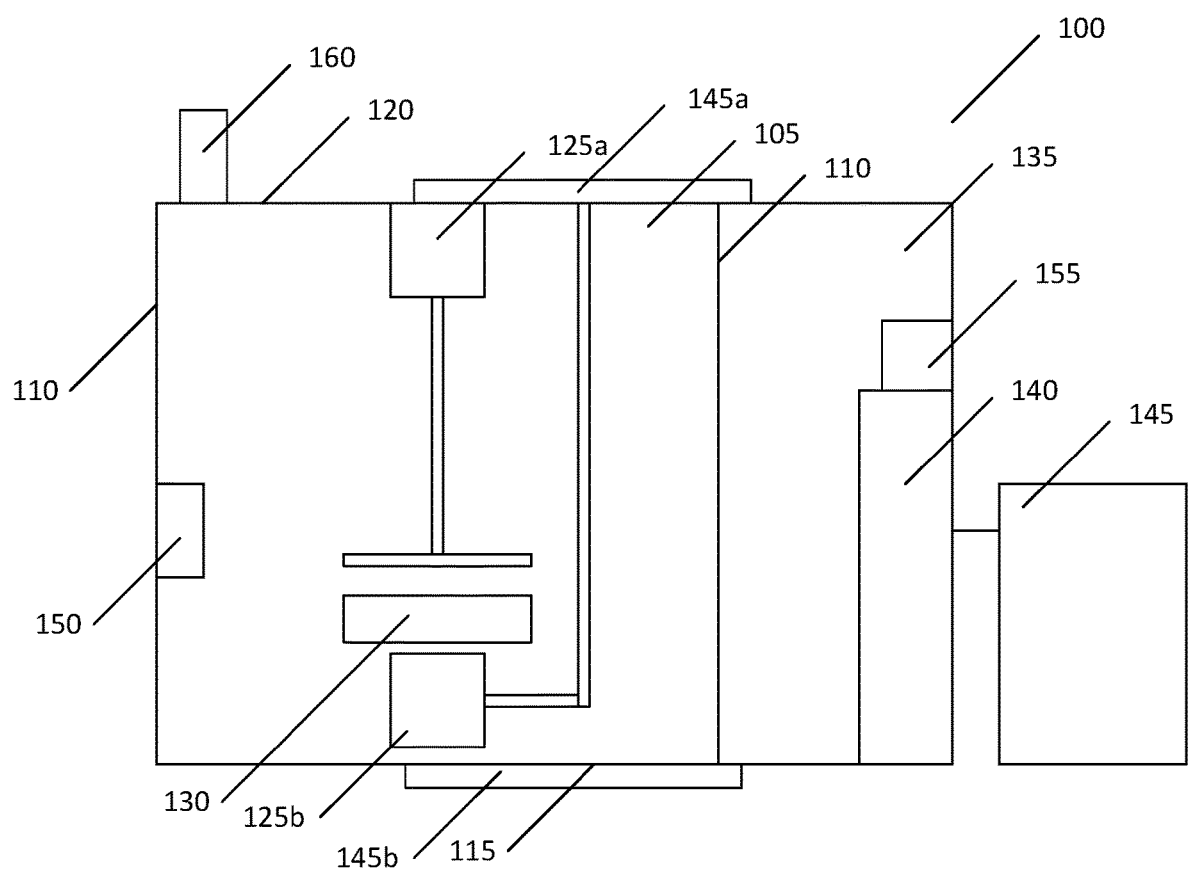
FIG. 3 illustrates a cross-section of another ambulatory surgical center according to certain embodiments of the present invention.

FIG. 3 illustrates a cross-section of another ambulatory surgical center according to certain embodiments of the present invention. FIG. 3 differs from FIG. 1 in that the radiating component 125b is shown fixed to ceiling 120 instead of the floor 115. Other implementations are also possible.

Certain embodiments may utilize a pre-existing office building or similar structure. Alternatively, certain embodiments can be provided as a kit or other modular assembly. For example, a hybrid operating room can be provided as a skid having pre-defined or standard interfaces to plumbing, power, medical gasses, power and signal conduits, and so on. Likewise, one or more doorways can be provided at a predetermined or standard location.

Certain embodiments, therefore, can include a standard plug interface to an operating room (OR) to provide plumbing hookups, air handling manifold, gas provision manifold, electrical hookups, and the like. The standard plug interface can combine multiple hookups that would traditionally be handled separately.

The hybrid operating room, whether implemented modularly or not, can include a neutralizing system for venting inhalation anesthesia or other bio-active gasses. In addition, or alternatively, the room can include an auxiliary interface to an external vent. As a further alternative, medical gasses can be returned to another room where they can be processed. These venting systems may be used, for example, in connection with using an anesthesia machine.

The hybrid operating room, whether implemented modularly or not, can include an internal wall structure for support of internal OR walls. The internal wall structure can include a cavity for insertion of radiation shielding. The cavity may be in the form of a mold to accommodate high density (HD) concrete or other materials. Other materials can include, for example, shotcrete, which is described in U.S. Pat. No. 6,565,647, or other materials that include metals embedded within concrete.

Internal walls of the room can have additional provisions for OR support. For example, the walls can have a contaminated/dirty supply pass-through for cleanup/autoclave. This supply can be segregated from clean/sterile supply.

Provision can also be made for endoscope handling, cleaning, sanitization, and storage in the room. Alternatively, such handling, cleaning, sanitization and storage could be performed in a nearby room.

The hybrid operating room can include a sterile supply cabinet. Optionally, this sterile supply cabinet can include a pass through for provisioning from an adjacent or adjoining room.

The sterile pass-through can include, for example, a conveyor belt and/or dumbwaiter. The sterile pass-through can include a sterile conveyor to a sterile room. Devices/supplies can be delivered to the room. The sterile pass-through may permit a nurse or other assistant to aid a doctor without leaving the room.

The hybrid operating room can be equipped with various cleaning features. For example, there can be built-in cleanup capability. There may be dispersion heads provided in the walls, ceiling, or floor for cleaning gas, liquid, plasma, light or other radiation agent. Additionally, the room may be provided with an automatic vent and/or exhaust for sanitization gas. The sanitization gas venting may be separate from the venting used for ordinary air changes.

The floor of the hybrid operating room may be provided with one or more accessible drains, for example in an elevated floor. The drains may be provided with a seal or valve to prevent contamination of the room through the drain when the drains are not being used.

A modular skid can potentially support several ORs in a modular fashion. For example, there can be a center section of a rose-shaped deployment of rooms. Alternatively, a modular skid can include just a single room.

Each room may be provided with features for power supply and handling. For example, each room may include breakers, fusing, and a line supply interface. Moreover, each room may include a safety cutoff switch interface. Additionally, each room may include transformers, a power supply, and line conditioners. Each room may also include a battery powered inverter and/or interface to external generator. Each room may further include an interface to an optional solar charger. The room can also be provided with full access for maintenance. Furthermore, the electrical systems can be provided with a proper grounding interface.

Each room may also include various computing and other electronic processing and information systems. For example, each room can be equipped with or connected to a computer network and/or server(s). Among other things, such computing devices may handle an imaging interface to OR and display/handling of data. The computing devices can include a built-in dedicated maintenance/inspection interface, tracking logs for maintenance, and automatic notification (for example, via email and/or short message service (SMS)) when an issue is detected. Issues can include, for example, power line spikes, service outages, battery charge state, low gas pressure, failed air handler, filter change time, or any other configured alert. The computing device may have comprehensive safety and operational monitoring performed automatically.

Each room may have various environmental controls. For example, the room may include an air handler and filters for air exchange.

Each room may be configured for gas provisioning. For example, the room can be configured for medical gasses, such as oxygen (for example, $O_2$), nitrous oxide $NO_2$, and anesthetic gas mixtures. As mentioned above, the rooms can also be configured to handle sanitizing gasses. Sanitizing gasses can include ethylene oxide, peroxides provided as aerosols, quaternary ammoniacals, or the like. The room may include suction and a waste trap.

The room can include access for maintenance. In certain embodiments, one or more of the walls may be a load bearing wall for shielding. In such a wall, or in another wall, there can be an access panel for maintenance/provisioning, such as gas cylinder exchange for gasses for the room.

Certain embodiments may provide a sliding horseshoe-shaped room with deployable shield doors. For example, the room may be generally u-shaped.

In certain embodiments, there may be an L-shaped building with one hallway, and multiple operating rooms, such as five ORs. There may be control room, which may be a section of the hybrid operating room or a separate room. For example, a control room may be provided next to the operating room or between two neighboring operating rooms. The control room may be, for example, about 250 to about 750 square feet.

Various imaging devices can be provided in the hybrid operating room. These imaging devices can include CAT scan, MRI, PET, Thorium scans, Lexi scans, or the like. As mentioned above, gamma knives can also be included. Proton therapy equipment can similarly be included.

Imaging and other devices can be fixed devices or mobile devices. For example, a fixed C-arm can be used. The fixed C-arm can be attached to the ceiling, to one or more of the walls, to the floor, or to any combination thereof.

Airflow in the room can be configured to be laminar. For example, the room can be configured to provide positive pressure in OR, being pushed from above. In air registers, there can be a central structural unistrut above with a track central to the air registers so laminar flow is not being interrupted. Sidewall laminar flow may alternatively be provided with air flowing across the surface of the operating table.

Certain embodiments can be designed to ensure verifiable quality care with specific requirements, such as the American Association for Accreditation of Ambulatory Surgery Facilities (AAAASF) standards that every facility may need to meet. The standards may include the following issues: general environment; operating room environment, policy and procedures; recovery room environment, policy and procedures; general safety in the facility; blood and medications; medical records; quality assessment/quality improvement; personnel; governance; and anesthesia.

Other features of the room may include adaptations to the imaging equipment. For example, the monitor for the imaging equipment may have a contactless user interface. For example, a viewer for film may permit a doctor to review various slides of film, to select a new film, to zoom a film, and the like without contact using gestures, eye-tracking, or voice commands.

The same contactless user interface, or a similar contactless user interface, can be used to control the c-arm or other mounting of the imaging device or other device.

Certain embodiments may include or one more microphone and or video recorder in the room. The recording equipment may be configured to permit a doctor to dictate an operation report as the operation is progressing. The recording may feature a voice-to-text feature and a playback from text feature, to permit the doctor to quickly review the transcription.

The system may also be configured to incorporate video and/or still images from a video or from the imaging device itself into in the operating report. Time stamps of the video and the dictated report may be used to automatically align the report and video or other images.

Voice control and other contactless user interfaces can also be used to control other aspects of the room. For example, such controls can be provided for control of lights, air change, medical gasses, or the like. Any recording equipment, dictation equipment, videography equipment, or the like may similarly be controlled without contact.

In certain embodiments the user interface may be any contactless interface. In addition to, or instead of that, controls can be done via a disposable clean surface. For example, a sterile plastic bag may be provided over each handle, screen or other contact-sensitive control element.

The hybrid operating room may be equipped with lighting. The lighting may include a spectrum-controllable lighting source to assist with visibility of surgical area. For example, red/green/blue (RGB) light emitting diode (LED) light sources can be provided. The color balance of these lights may be programmable, and may be configured to assist with visualizing certain tissues or samples. For example, a color of lighting can be altered to assist with identifying a particular expected color in an image or tissue.

In certain embodiments there can be natural lighting enhancement through redirected fiber-optic fixtures. There may be a light receiver outside and a light emitter inside surgical room at desired locations, ambient diffused or through collimated surgical light beams. Alternatively, or in addition, programmable lighting may be configured to simulate actual or desired outdoor lighting conditions, including changes in color or intensity over time.

A backup lighting source can be provided by natural illumination routing, such as fiber optic, waveguide, or reflector tunnel. The backup lighting source be configured to include a closable aperture to adjust ambient light in the surgical center.

The above discussion provided an ASC as an example of a non-hospital building that could be configured according to certain embodiments of the present invention. An office-based lab (OBL) is another example of such a building that may be equipped with certain embodiments of the present invention. A hybrid procedure room in an OBL may be equipped similarly to the way in which a hybrid operating room in an ASC is equipped, as described above. In certain cases, however, an OBL may not be equipped to perform general anesthesia. Thus, for example, there may not be a need to have a medical gasses section to the hybrid procedure room.

One having ordinary skill in the art will readily understand that the invention as discussed above may be practiced with steps in a different order, and/or with hardware elements in configurations which are different than those which are disclosed. Therefore, although the invention has been described based upon these preferred embodiments, it would be apparent to those of skill in the art that certain modifications, variations, and alternative constructions would be apparent, while remaining within the spirit and scope of the invention. In order to determine the metes and bounds of the invention, therefore, reference should be made to the appended claims.

I claim:

1. A stationary ambulatory surgical center, the stationary ambulatory surgical center comprising:
a plurality of hybrid operating rooms, wherein each of the hybrid operating rooms comprises radiation-shielded walls, a floor, and a ceiling;
an imaging device disposed in a central area of each hybrid operating room;
an operating table disposed in the central area of each hybrid operating room; and
a door connecting each hybrid operating room to a hallway,
wherein the stationary ambulatory surgical center is in a building constructed to conform to International Building Code (IBC) Group B classification standards.

2. The stationary ambulatory surgical center of claim 1, wherein the imaging device comprises a fixed c-arm device.

3. The stationary ambulatory surgical center of claim 2, wherein the fixed c-arm device is fixed to the ceiling.

4. The stationary ambulatory surgical center of claim 1, wherein the ambulatory surgical center excludes an inpatient room configured for stay of patients for at least twenty-four hours.

5. The stationary ambulatory surgical center of claim 1, wherein the ambulatory surgical center is not adjacent to or within a hospital.

6. The stationary ambulatory surgical center of claim 1, further comprising:
a central medical gas room configured to provide gas, suction, or both gas and suction to the plurality of hybrid operating rooms.

7. A building comprising an ambulatory surgical center, the ambulatory surgical center comprising:

a plurality of hybrid operating rooms, wherein each of the hybrid operating rooms comprises radiation-shielded walls, a floor, and a ceiling;
a fixed c-arm device disposed in a central area of each hybrid operating room;
an operating table disposed in the central area of each hybrid operating room; and
a door connecting each hybrid operating room to a hallway,
wherein the building is constructed of combustible construction materials.

8. The building of claim 7, wherein the building comprises a stationary structure.

9. The building of claim 7, wherein the ambulatory surgical center excludes an inpatient room configured for stay of patients for at least twenty-four hours.

10. The building of claim 7, wherein the building is not adjacent to or within a hospital.

11. The building of claim 7, further comprising:
a central medical gas room configured to provide gas, suction, or both gas and suction to the plurality of hybrid operating rooms.

12. The building of claim 7, wherein the plurality of hybrid operating rooms are on a ground floor of the building.

13. A building comprising an ambulatory surgical center, the ambulatory surgical center comprising:
a plurality of hybrid operating rooms, wherein each of the hybrid operating rooms comprises radiation-shielded walls, a floor, and a ceiling;
an imaging device disposed in a central area of each hybrid operating room;
an operating table disposed in the central area of each hybrid operating room; and
a door connecting each hybrid operating room to a hallway,
wherein the building is constructed to conform to International Building Code (IBC) Group B standards.

14. The building of claim 13, wherein the imaging device is fixed to the ceiling.

15. The building of claim 13, wherein the building comprises a stationary structure.

16. The building of claim 13, wherein the ambulatory surgical center excludes an inpatient room configured for stay of patients for at least twenty-four hours.

17. The building of claim 13, wherein the building is not adjacent to or within a hospital.

18. The building of claim 13, wherein the plurality of hybrid operating rooms are on a ground floor of the building.

19. A building comprising a stationary ambulatory surgical center, the stationary ambulatory surgical center comprising a plurality of hybrid operating rooms, wherein each of the hybrid operating rooms comprises:
radiation shielded walls, a floor, and a ceiling;
an imaging device disposed in a central area of each hybrid operating room; and
an operating table disposed in the central area of each hybrid operating room, wherein the ambulatory surgical center excludes an inpatient room configured for stay of patients for at least twenty-four hours.

20. The building of claim 19, wherein the imaging device is fixed to the ceiling.

21. The building of claim 19, wherein the building is not adjacent to or within a hospital.

22. The building of claim 19, wherein the plurality of hybrid operating rooms are on a ground floor of the building.

23. A stationary ambulatory surgical center, the stationary ambulatory surgical center comprising:
a plurality of hybrid operating rooms, wherein each of the hybrid operating rooms comprises radiation-shielded walls, a floor, and a ceiling;
an imaging device disposed in a central area of each hybrid operating room;
an operating table disposed in the central area of each hybrid operating room; and
a door connecting each hybrid operating room to a hallway,
wherein the stationary ambulatory surgical center is in a building.

24. A building comprising an ambulatory surgical center, the ambulatory surgical center comprising:
a hybrid operating room, the hybrid operating room comprising radiation-shielded walls, a floor, and a ceiling;
an imaging device disposed in a central area of the hybrid operating room;
an operating table disposed in the central area of the hybrid operating room; and
a door connecting the hybrid operating room to a hallway.

* * * * *